United States Patent [19]

Ferrari

[11] Patent Number: 4,890,622

[45] Date of Patent: Jan. 2, 1990

[54] DISPOSABLE BIOMEDICAL ELECTRODE

[76] Inventor: Robert K. Ferrari, 100 S. 13th St., P.O. Box 578, Herrin, Ill. 62948

[21] Appl. No.: 263,372

[22] Filed: Oct. 27, 1988

[51] Int. Cl.$^4$ ............................................... A61B 5/04
[52] U.S. Cl. .................................................... 128/640
[58] Field of Search ............... 128/639, 640, 798, 802, 128/803

[56] References Cited

U.S. PATENT DOCUMENTS

| | | |
|---|---|---|
| 4,274,420 | 6/1981 | Hymes . |
| 4,391,278 | 7/1983 | Cahalan et al. . |
| 4,522,211 | 6/1985 | Bare et al. . |
| 4,524,087 | 6/1985 | Engel . |
| 4,539,996 | 9/1985 | Engel . |
| 4,543,958 | 10/1985 | Cartmell . |
| 4,554,924 | 11/1985 | Engel ................................. 128/640 |
| 4,679,564 | 7/1987 | Sessions ............................. 128/640 |
| 4,694,835 | 9/1987 | Strand ................................ 128/640 |
| 4,706,680 | 11/1987 | Keusch et al. ..................... 128/640 |
| 4,798,208 | 1/1989 | Faasse, Jr. .......................... 128/640 |

Primary Examiner—Lee S. Cohen
Attorney, Agent, or Firm—Vernon J. Pillote

[57] ABSTRACT

A disposable biomedical electrode of the type adapted for connection by a clip-on connector to a lead wire, comprising a semi-flexible composite sheet member having a non-conductive upper layer and an electrically conductive current distributing lower layer, and a layer of biomedical electrically conductive pressure sensitive adhesive on an electrode section of the sheet. A layer of resilient foamed plastic is fixed on the non-conductive upper layer of the electrode, on a portion of the tab section of the semi-flexible sheet, to enhance gripping of the tab section by the clip-on type connector assembly.

5 Claims, 1 Drawing Sheet

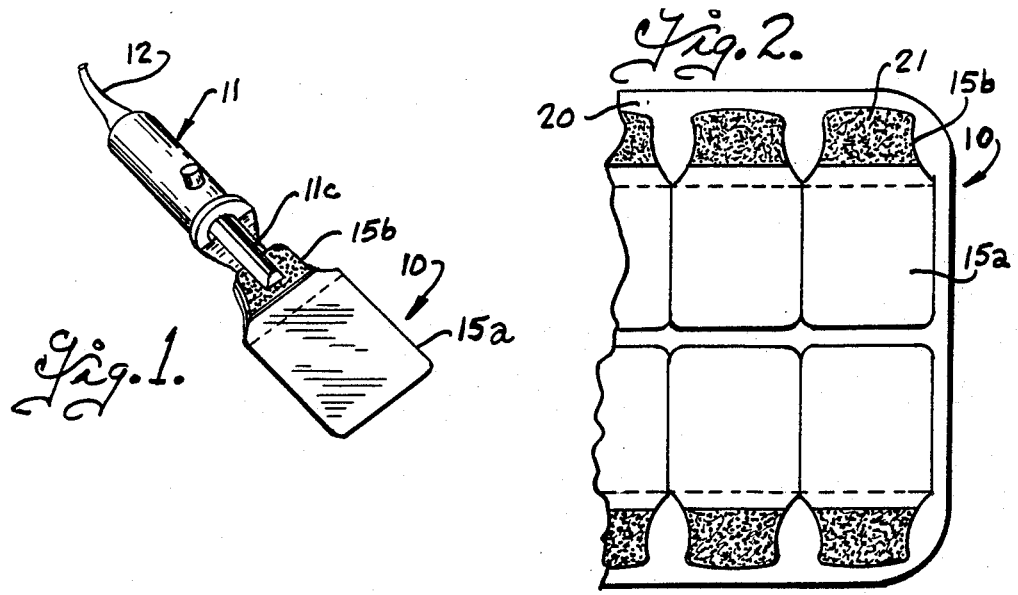
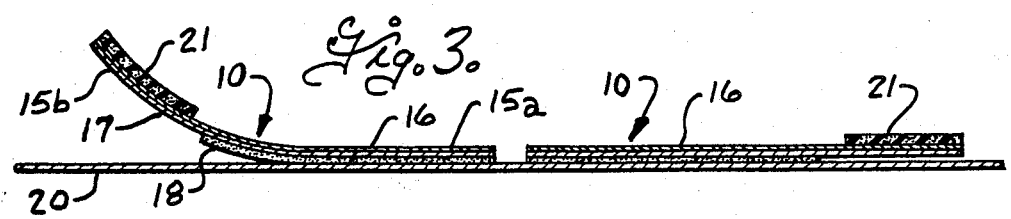
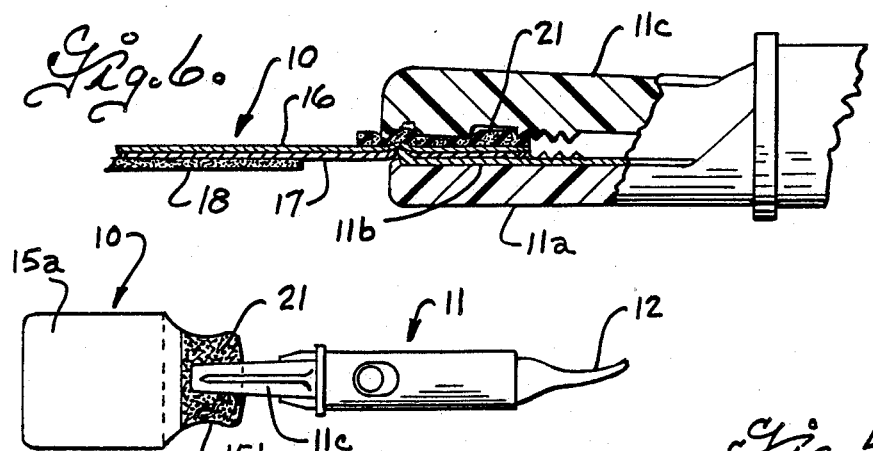
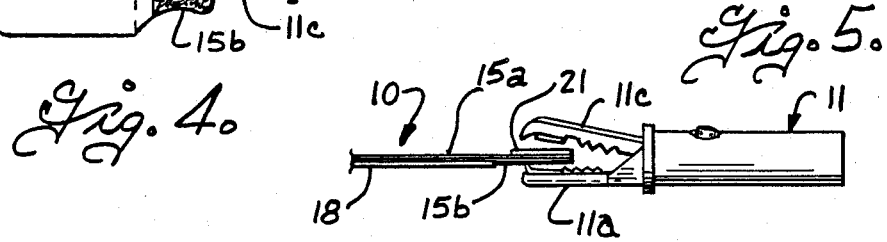

DISPOSABLE BIOMEDICAL ELECTRODE

BACKGROUND OF THE INVENTION

Disposable biomedical electrodes have heretofore been made with an integral tab adapted for connection by a clip-on connector assembly to a lead wire, some examples of which are disclosed in U.S. Pat. Nos. 4,522,211; 4,524,087; 4,539,996 and 4,543,958. The clip-on connector assemblies are reused many times and the gripping action of the clip-on connectors tends to weaken with usage. Weakening of the clip-on connector adversely affects the electrical contact between the electrode tab and the connector and can result in erratic transmission of signals from the electrode, particularly upon patient movement or movement of the lead wires.

SUMMARY OF THE INVENTION

It is an object of the present invention to provide a disposable biomedical electrode of the type adapted for connection by a clip-on connector assembly to a lead wire, and which enhances gripping of the tab section by the clip-on type connector to provide improved transmission of signals from the electrode to the lead wires.

Accordingly, the present invention provides a disposable biomedical electrode comprising a flexible composite sheet member having a non-conductive upper layer and an electrically conductive lower current distributing layer, the sheet member having an electrode section and an integral tab section and a layer of biomedically conductive pressure sensitive adhesive on the lower current distributing layer of the sheet member only on the electrode section so that the conductive lower current distributing layer remains exposed on the tab section. A layer of resilient foamed plastic is fixed on the non-conductive upper layer of the electrode, on at a least a portion of the tab section of the semi-flexible sheet, to enhance gripping of the tab section by the clip-on type connector assembly.

The layer of foamed plastic has nominal thickness substantially greater than the thickness of the semi-flexible sheet member and a compressibility substantially greater than the compressibility of the semi-flexible sheet member. The layer of resilient foamed plastic is advantageously provided only on a portion of the tab section that is spaced from the electrode section to facilitate flexing of the tab section intermediate the electrode section and the layer of foamed plastic.

DETAILED DESCRIPTION OF THE DRAWINGS

FIG. 1 is a perspective view of a biomedical electrode of the present invention with a clip-on connector attached thereto;

FIG. 2 is a fragmentary plan view of a release liner card having a plurality of biomedical electrodes thereon;

FIG. 3 is a fragmentary sectional view through the card of electrodes on a larger scale than FIG. 2, and illustrating one of the electrodes partially removed from the card;

FIG. 4 is a plan view of a biomedical electrode of the present invention with a clip-on connector applied thereto;

FIG. 5 is a fragmentary side view illustrating attachment of the clip-on connector to the electrode; and FIG. 6 is a fragmentary sectional view on an enlarged scale, illustrating the clip-on connector applied to the tab section of the electrode.

DETAILED DESCRIPTION

The disposable biomedical electrode of the present invention, designated generally by the numeral 10, is of the type adapted for connection by a clip-on type connector assembly 11, to a lead wire 12, and is particularly adapted for use as a sensing or monitoring electrode such as in ECG or EEG tests.

The electrode 10 comprises a semi-flexible composite sheet member having a non-conductive upper layer 16 and a conductive lower current distributing layer 17 at a lower side. The semi-flexible sheet member has an electrode section 15a and an integral tab section 15b, and a layer 18 of biomedical electrically conductive, pressure sensitive adhesive adhered to the lower current distributing layer 17 of the sheet member, only on the electrode section 15a of the sheet member, so that the conductive lower distributing layer remains exposed on the tab section 15b. As is conventional, a release liner sheet 20 is applied to face of the pressure sensitive adhesive layer, to protect the adhesive prior to application of the electrode to the skin of a patient.

As used herein, the term semi-flexible composite sheet member refers to a sheet member that is thin and sufficiently flexible to conform to the contours of the skin to which it is applied, but which is not subject to significant stretching or permanent deformation during normal use or when removing the electrode from the backing sheet 20. The semi-flexible composite sheet member can be formed of a thin flexible sheet of metal foil with a thin flexible sheet of non-conductive plastic laminated thereto or a thin flexible coating of non-conductive material applied to one side. The semi-flexible composite sheet member can also be formed of a semi-flexible sheet of non-conductive plastic such as a polyester sold under the trademark "Mylar", with an electrically conductive coating or ink applied to one side to provide the electrically conductive surface 17. In a presently preferred embodiment, the electrode is formed of a thin sheet of polyvinylchloride of the order of 3 to 5 mils thickness, with a thin sheet or foil of abraded tin of the order of 1 to 2 mils thickness adhered to one side of the vinyl sheet.

Various different biomedical, electrically conductive pressure sensitive adhesives, for example as disclosed in U.S. Pat. Nos. 4,274,420; 4,391,278; 4,524,087 and 4,543,598, can be used to form the electrically conductive adhesive layer 18 on the electrode section of the composite sheet. A presently preferred skin compatible electrically conductive pressure sensitive adhesive is marketed by Medtronic, Inc. under the trademark "Promeon" No. RG 63b. As previously described, the electrically conductive adhesive is applied only to the electrode section 15a of the composite sheet member so that the electrically conductive current distributing layer 17 remains exposed at the underside of the tab section 15b. Thus, the tab section can be lifted after the electrode section is applied to the skin of the patient, to facilitate application of the connector assembly 11 thereto and to avoid contamination of the connector assembly by the pressure sensitive adhesive.

In accordance with the present invention, a layer of resilient foamed plastic 21 is fixed on the non-conductive upper layer of the electrode, on a portion of the tab section 15b of the semi-flexible sheet. The foamed layer 21 has a thickness substantially greater than the thickness of the sheet member 15 and a compressibility substantially greater than the compressibility of the sheet member, such that the jaws of the clip-on connector can compress and bite into the layer of foamed plastic under the jaw closing pressure. The foamed layer 21 is preferably formed of medium or high density cross-linked polyethylene foam having a thickness of about 1/32" to 1/16" and be attached to the tab section by a suitable adhesive. The foamed layer may, for example, be formed of a flexible closed-cell polyethylene copolymer foam marketed under the trademark VOLORA type E, by the Voltek division of Sekisui America Corp., Lawrence, Mass., and having a density of 2 to 6 pounds per cubic foot. It is also contemplated that the foamed layer could be of low density foam material such as polyurethene foam, and that the foam thickness could be increased.

The layer of foamed plastic 21 is preferably applied on only a portion of the tab section 15b that is spaced along the tab section in a direction away from the pressure sensitive adhesive 18 on the electrode section, to facilitate flexing of the tab section in the area intermediate the electrode section and the layer of resilient foamed plastic.

The clip-on type connector assembly 11 can be of various different conventional constructions and may, for example, be of the type commonly referred to as "alligator" clips. The clip-on connectors commonly have a lower jaw 11a with an electrically conducted member 11b (FIG. 6) and an upper jaw 11c that is yieldably biased by resilient means such as a spring (not shown) toward the lower jaw to a closed position. At least one and commonly both of the lower and upper jaws 11a and 11c are provided with teeth to enhance gripping of the tab section of the electrodes. However, the clip-on connectors are commonly reused many times and the springs or other resilient means for yieldably urging the upper and lower jaws relative to each other to a closed position, become weakened with repeated usage. The resilient foamed plastic layer 21 is selected so as to have a compressibility such as to be substantially compressed by the resilient closing pressures between the upper and lower jaws. This enhances gripping action of the tab section 15b of the electrode between the jaws of the connector assembly and resiliently presses the conductive current distributing layer at the underside of the tab section against the conductive member 11b on the lower jaw.

As previously described, a release liner 20 may be applied to the lower side of the pressure sensitive adhesive layer 18 to preserve the adhesive character of the layer until ready for use. Such release liners are well known and may, for example, be a silicone coated paper.

The electrodes can be economically fabricated. A strip of non-conductive plastic such as polyvinylchloride is laminated to a strip of metal foil such as tin, by a suitable adhesive, to form a composite strip. A strip of electrically conductive pressure sensitive adhesive is then applied in a band somewhat narrower than the width of the composite strip, to the metal foil side of the composite strip in an area corresponding to what will become the electrode section of the sheet member, and a strip of foamed plastic is applied in a narrow band along a portion of the strip that will become the tab section of the electrode. A strip forming the backing sheet 20 and having a width greater than the width of the composite sheet, is applied to the exposed side of the pressure sensitive adhesive. The electrodes are then cut, as by running the composite strip through a rotary die cutter which is arranged to cut through the composite strip and adhesive layer and foam strip, but not completely through the backing strip. The scrap is then removed leaving the finished electrodes on the backing strip.

The embodiments of the invention in which an exclusive property or privilege is claimed are defined as follows:

1. A disposable biomedical electrode of the type adapted for connection by a clip-on connector assembly to a lead wire, comprising, a semi-flexible composite sheet member having a non-conductive upper layer at an upper side and a conductive lower current distributing layer at a lower side, the semi-flexible sheet member having an electrode section and an integral tab section, a layer of biomedical electrically conductive, pressure sensitive adhesive adhered to the conductive lower current distributing layer of the sheet member only on the electrode section such that the conductive lower current distributing layer remains exposed on the tab section, the improvement comprising a layer of resilient foamed plastic fixed on the non-conductive upper layer of the electrode on only a portion of the tab section of the semi-flexible sheet member that is spaced along the tab section in a direction away from the pressure sensitive adhesive on the electrode section to enhance gripping of the tab section by the clip-on type connector assembly and facilitate flexing of the tab section in the area intermediate the electrode section and the layer of resilient foamed plastic.

2. A disposable biomedical electrode according to claim 1 wherein said layer of resilient foamed plastic has a nominal thickness substantially greater than the thickness of said semi-flexible sheet member and a compressibility substantially greater than the compressibility of said semi-flexible sheet member.

3. A disposable biomedical electrode according to claim 2 wherein said layer of resilient foamed plastic comprises a closed cell polyethylene copolymer having a density of 2 to 6 pounds per cubic foot.

4. A disposable biomedical electrode according to claim 1 wherein said semi-flexible sheet member comprises an upper sheet of non-conductive plastic material and a lower layer of electrically conductive material.

5. A disposable biomedical electrode according to claim 1 wherein said semi-flexible sheet member comprises an upper sheet of non-conductive plastic material and a lower sheet of electrically conductive metal adhered to the upper sheet.

* * * * *